United States Patent
Wang et al.

(10) Patent No.: US 11,819,711 B2
(45) Date of Patent: Nov. 21, 2023

(54) RADIOTHERAPY SYSTEM, AND DEVICE AND METHOD FOR VERIFYING SAME

(71) Applicant: OUR UNITED CORPORATION, Xi'an (CN)

(72) Inventors: Wen Wang, Xi'an (CN); Hao Yan, Xi'an (CN); Tianchang Gou, Xi'an (CN); Jinsheng Li, Xi'an (CN); Jiuliang Li, Xi'an (CN); Fan Gao, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 263 days.

(21) Appl. No.: 17/432,901

(22) PCT Filed: Feb. 21, 2019

(86) PCT No.: PCT/CN2019/075761
§ 371 (c)(1),
(2) Date: Aug. 20, 2021

(87) PCT Pub. No.: WO2020/168525
PCT Pub. Date: Aug. 27, 2020

(65) Prior Publication Data
US 2022/0203131 A1 Jun. 30, 2022

(51) Int. Cl.
*A61N 5/10* (2006.01)
(52) U.S. Cl.
CPC ......... *A61N 5/1049* (2013.01); *A61N 5/1075* (2013.01); *A61N 2005/1076* (2013.01)
(58) Field of Classification Search
CPC ............... A61N 5/1049; A61N 5/1075; A61N 2005/1076
See application file for complete search history.

(56) References Cited

U.S. PATENT DOCUMENTS

| 8,565,377 B2 | 10/2013 | Robar et al. |
| 8,712,011 B2 | 4/2014 | Robar et al. |

(Continued)

FOREIGN PATENT DOCUMENTS

| CN | 200951265 Y | 9/2007 |
| CN | 201936015 U | 8/2011 |

(Continued)

OTHER PUBLICATIONS

China National Intellectual Property Administration, Notification to grant patent right for invention of Chinese application No. 201980000893.0 dated Jun. 21, 2022, which is foreign counterpart application of this US application.

(Continued)

*Primary Examiner* — Blake C Riddick
(74) *Attorney, Agent, or Firm* — Knobbe, Martens, Olson & Bear, LLP

(57) ABSTRACT

Provided is a device for verifying a radiotherapy system, including at least two of a first verification phantom, a second verification phantom, and a third verification phantom, wherein a slot for holding a film is provided in the first verification phantom, a first positioning member is disposed at a center of the second verification phantom, a second positioning member is disposed at a center of the third verification phantom, and a center point of the first verification phantom, a center point of the first positioning member and a center point of the second positioning member are coaxial.

20 Claims, 8 Drawing Sheets

(56) References Cited

U.S. PATENT DOCUMENTS

| | | |
|---|---|---|
| 2004/0120560 A1 | 6/2004 | Robar et al. |
| 2006/0002519 A1 | 1/2006 | Jenkins et al. |
| 2007/0165779 A1* | 7/2007 | Chen .................. A61N 5/1049 378/65 |
| 2008/0219410 A1* | 9/2008 | Gunzert-Marx ..... A61N 5/1048 378/207 |
| 2008/0219411 A1* | 9/2008 | Gunzert-Marx ..... A61N 5/1048 250/252.1 |
| 2012/0230462 A1 | 9/2012 | Robar et al. |
| 2014/0031603 A1 | 1/2014 | Robar et al. |
| 2015/0085993 A1 | 3/2015 | Scheib |
| 2015/0139513 A1* | 5/2015 | Niu .......................... G06T 7/66 382/131 |
| 2017/0050052 A1* | 2/2017 | Burgett .................. B33Y 80/00 |
| 2018/0339173 A1* | 11/2018 | Kilby .................. A61N 5/1083 |
| 2019/0001156 A1* | 1/2019 | Tulik .................. A61N 5/1081 |
| 2019/0175951 A1* | 6/2019 | Yu ......................... A61B 6/032 |
| 2019/0329072 A1* | 10/2019 | Magro ................. A61N 5/1071 |
| 2020/0061392 A1* | 2/2020 | Filiberti ............... A61N 5/1045 |
| 2020/0129785 A1* | 4/2020 | Li ....................... A61N 5/1075 |
| 2020/0289850 A1* | 9/2020 | Wösle .................. A61N 5/1075 |
| 2020/0346042 A1* | 11/2020 | Maltz ................... G06T 7/0012 |
| 2020/0359988 A1* | 11/2020 | Woods .................... A61B 6/08 |
| 2021/0128951 A1* | 5/2021 | Mead ..................... A61B 6/582 |

FOREIGN PATENT DOCUMENTS

| | | |
|---|---|---|
| CN | 203138520 U | 8/2013 |
| CN | 103353602 A | 10/2013 |
| CN | 203483752 U | 3/2014 |
| CN | 203802968 U | 9/2014 |
| CN | 104415459 A | 3/2015 |
| CN | 105233427 A | 1/2016 |
| CN | 205460526 U | 8/2016 |
| CN | 105983182 A | 10/2016 |
| CN | 206252739 U | 6/2017 |
| CN | 206381505 U | 8/2017 |
| CN | 108525140 A | 9/2018 |
| CN | 208243929 U | 12/2018 |
| CN | 208405799 U | 1/2019 |
| CN | 109350865 A | 2/2019 |
| EP | 1967231 A1 | 9/2008 |
| JP | 2011239830 A | 12/2011 |
| KR | 20100111985 A | 10/2010 |
| KR | 20120079726 A | 7/2012 |
| WO | 2012053770 A2 | 4/2012 |

OTHER PUBLICATIONS

Jia Weijuan et al., Simulator and Block Carriage Based Treatment Simulation Before Radiotherapy, Chinese Journal of Medical Physics, vol. 31. No. 1, Jan. 31, 2014, entire document.

First office action of Chinese application No. 202010398582.9 dated Aug. 18, 2021.

First office action of Chinese application No. 201980000893.0 dated Dec. 10, 2021.

International search report of PCT application No. PCT/CN2019/075761 dated May 30, 2019.

* cited by examiner

RADIOTHERAPY SYSTEM, AND DEVICE AND METHOD FOR VERIFYING SAME

This application is a U.S. National Phase Application of International Application No. PCT/CN2019/075761, filed on Feb. 21, 2019, the content of which is herein incorporated by reference in its entirety.

TECHNICAL FIELD

The present disclosure relates to the field of radiotherapy technologies, and in particular, relates to a radiotherapy system and a device and method for verifying the same.

BACKGROUND

A radiotherapy system generally includes: a rotating gantry and a treatment head disposed on the rotating gantry. Rays emitted from the treatment head can be used to treat a patient at a target point on an affected part. Under normal circumstances, a beam focus (i.e., an isocenter of treatment) of the rays emitted from the treatment head should be in coincidence with an isocenter of mechanical rotation of the rotating gantry. When the target point is positioned at a position of the isocenter of mechanical rotation, the beam focus can accurately irradiate the target point, thereby realizing precise treatment. However, due to installation errors and other reasons, there may be a deviation between the isocenter of treatment and the isocenter of mechanical rotation. Here, if the target point is positioned to the isocenter of mechanical rotation, the beam focus may not accurately irradiate the position of the target point, such that the precise treatment cannot be realized.

SUMMARY

The present disclosure provides a radiotherapy system and a device and method for verifying the same. The technical solutions are as follows.

In an aspect, a device for verifying a radiotherapy system is provided. The device includes at least two of a first verification phantom, a second verification phantom, and a third verification phantom;

wherein a slot for holding a film is provided in the first verification phantom, a first positioning member is disposed at a center of the second verification phantom, a second positioning member is disposed at a center of the third verification phantom, and a center point of the first verification phantom, a center point of the first positioning member and a center point of the second positioning member are coaxial.

Optionally, the slots include: a first slot and a second slot; and an insertion surface of the first slot is perpendicular to an insertion surface of the second slot, and a center point of the insertion surface of the first slot and a center point of the insertion surface of the second slot are both in coincidence with the center point of the first verification phantom.

Optionally, an opening of the first slot and an opening of the second slot are both disposed on a first outer surface of the first verification phantom.

Optionally, the first verification phantom is provided with a first through hole for communicating an outer surface of the first verification phantom with the first slot, and a second through hole for communicating the outer surface of the first verification phantom with the second slot;

an extending direction of the first through hole intersects with the insertion surface of the first slot, and an intersection point of the first through hole and the insertion surface of the first slot is the center point of the insertion surface of the first slot; and an extending direction of the second through hole intersects with the insertion surface of the second slot, and an intersection point of the second through hole with the insertion surface of the second slot is the center point of the insertion surface of the second slot.

Optionally, an outer surface of the second verification phantom is provided with at least three sets of calibration lines, each set of the calibration lines includes two calibration lines perpendicular to each other, an intersection point of the two calibration lines included in each set of the calibration lines is a target point, and the respective target points of the at least three sets of calibration lines are coplanar; and wherein among the at least three sets of calibration lines, two sets of the calibration lines are respectively disposed on two opposite side surfaces of the second verification phantom, and one set of the calibration lines is disposed at a surface, distal from a support that is configured to support the second verification phantom, of the second verification phantom.

Optionally, a plurality of third positioning members are further disposed within the second verification phantom; and the plurality of third positioning members are non-coplanar, and a number of the third positioning members is not less than 4.

Optionally, distances between any two of the third positioning members are equal, and distances between each of the third positioning members and the first positioning member are equal.

Optionally, the first positioning member and the third positioning members are both made of at least one of aluminum, Teflon, glass, or ceramic.

Optionally, the third verification phantom is an internally hollow housing, within which a second positioning member pipe is disposed, and the second positioning member is disposed within the second positioning member pipe.

Optionally, a housing of the first verification phantom is made of organic glass; and/or, a housing of the second verification phantom is made of organic glass; and/or, a housing of the third verification phantom is made of organic glass.

Optionally, the second positioning member is made of tungsten.

Optionally, in a case where the device includes the third verification phantom, the third verification phantom is detachably connected with the first verification phantom or the second verification phantom.

Optionally, the device for verifying the radiotherapy system includes: the first verification phantom, the second verification phantom, and the third verification phantom, wherein the first verification phantom, the second verification phantom, and the third verification phantom are sequentially disposed along a length direction of a treatment couch.

Optionally, the device for verifying the radiotherapy system further includes: a base, wherein at least one of the first verification phantom, the second verification phantom, or the third verification phantom is disposed on the base.

In another aspect, a radiotherapy system is provided. The radiotherapy system includes: the device for verifying the radiotherapy system as described in the aspects above.

In a further aspect, a method for verifying a radiotherapy system is provided. The method includes:

at least one of a first verification process, a second verification process, or a third verification process,
wherein the first verification process includes:
acquiring a first image and a second image, wherein the first image and the second image are obtained by respectively irradiating two films inserted in slots of a first verification phantom with a beam and then scanning the two irradiated films respectively; and
determining, based on the first image and the second image, actual coordinates of a beam focus of the beam, and determining, based on the actual coordinates of the beam focus, a deviation of an isocenter of treatment from an isocenter of mechanical rotation,
the second verification process includes:
adjusting a position of a second verification phantom, such that a first positioning member disposed at a center of the second verification phantom is aligned with an isocenter of mechanical rotation;
acquiring at least two third images, wherein each of the third images is obtained by performing image capture on the first positioning member; and
determining a deviation of the isocenter of mechanical rotation based on first coordinates of the first positioning member in each of the third images and reference coordinates of a center point in each of the third images, and
the third verification process includes:
acquiring at least two fourth images, wherein the fourth images are obtained by irradiating a second positioning member disposed at a center of a third verification phantom with a beam and then performing image capture;
determining, based on each of the fourth images as obtained, actual coordinates of a beam focus, and determining, based on the actual coordinates of the beam focus, a deviation of an isocenter of treatment from the isocenter of mechanical rotation.

In a further another aspect, a device for verifying a radiotherapy system is provided. The device includes:

a processor and a memory storing instructions therein, wherein the instructions, when loaded and executed by the processor, cause the processor to execute the method for verifying the radiotherapy system as described in the aspects above.

In a further another aspect, a storage medium is provided. The storage medium stores instructions therein, wherein the storage medium, when being operated on a processing component, causes the processing component to execute the method for verifying the radiotherapy system as described in the aspects above.

It should be understood that both the foregoing general description and the following detailed description are merely examples and explanatory, and are not intended to limit the present disclosure.

BRIEF DESCRIPTION OF THE DRAWINGS

To describe the technical solutions in the embodiments of the present disclosure more clearly, the following briefly introduces the accompanying drawings required for describing the embodiments. Apparently, the accompanying drawings in the following description show merely some embodiments of the present disclosure, and a person of ordinary skills in the art may still derive other drawings from these accompanying drawings without creative efforts.

The embodiments of the present disclosure have been illustrated explicitly through the drawings above, and will be described in more detail below. These drawings and text descriptions are not intended to limit the scope of the inventive conception in any way, but to explain the concept of the present disclosure to persons of skills in the art by referring to particular embodiments.

DETAILED DESCRIPTION

To present the objects, technical solutions and advantages of the present disclosure more clearly, the embodiments of the present disclosure will be described in further detail with reference to the accompanying drawings.

In the related art, in order to ensure the accuracy of radiotherapy, a device for verification of the deviation between the isocenter of treatment and the isocenter of mechanical rotation is provided, such as the MIMI phantom. Before the radiotherapy is administered, this device for verification may be configured to verify whether the isocenter of treatment is in coincidence with the isocenter of mechanical rotation (that is, whether a deviation exists). When a deviation exists between the isocenter of treatment and the isocenter of mechanical rotation, the position of a treatment couch can be adjusted in time based on the deviation, thereby improving the coincidence accuracy between the isocenter of mechanical rotation and an isocenter of device.

However, the device for verification in the related art has a single function and can only verify whether the isocenter of mechanical rotation is in coincidence with the isocenter of device.

Figure 1:
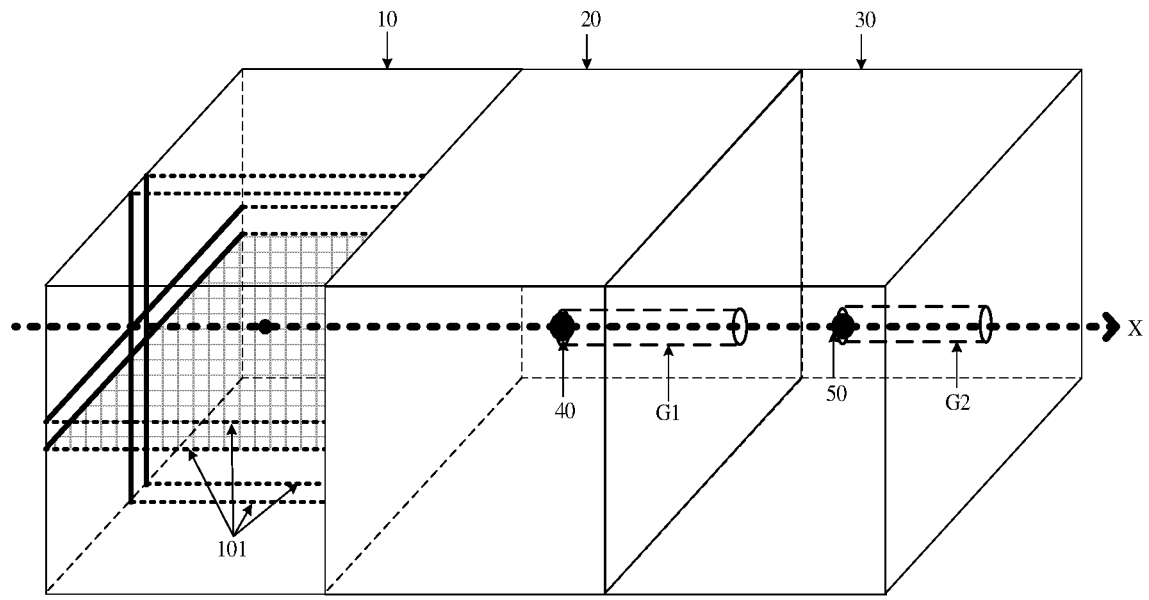
FIG. 1 is a schematic structural diagram of a device for verifying a radiotherapy system according to an embodiment of the present disclosure.

FIG. 1 is a schematic structural diagram of a device for verifying a radiotherapy system according to an embodiment of the present disclosure. As illustrated in FIG. 1, the device for verifying the radiotherapy system may include: at least two of a first verification phantom 10, a second verification phantom 20 and a third verification phantom 30. For example, the device for verifying the radiotherapy system illustrated in FIG. 1 includes: the first verification phantom 10, the second verification phantom 20 and the third verification phantom 30.

Referring to FIG. 1, a slot 101 for holding a film is provided in the first verification phantom 10, a first positioning member 40 is disposed at a center of the second verification phantom 20, and a second positioning member 50 is disposed at a center of the third verification phantom 30. Moreover, a center point of the first verification phantom 10, a center point of the first positioning member 40, and a center point of the second positioning member 50 are coaxial. That is, the center point of the first verification phantom 10, the center point of the first positioning member 40 and the center point of the second positioning member 50 are disposed on a same axis, for example, an axis X illustrated in FIG. 1.

Optionally, both the first verification phantom 10 and the third verification phantom 30 are configured to verify a deviation between an isocenter of treatment and an isocenter of mechanical rotation. The isocenter of treatment is also referred to as an isocenter of nuclear physics. The second verification phantom 20 is configured to implement at least one of the following functions: verifying a deviation of the isocenter of mechanical rotation, calibrating geometric parameters (for example, detecting whether a position of a laser light is deviated, verifying an installation error of an image capture component, etc.) or verifying the accuracy in image-guided positioning.

In a case where the device for verifying the radiotherapy system includes the first verification phantom and the second verification phantom, or the second verification phantom and the third verification phantom, or the first verification phantom, the second verification phantom and the third verification phantom, which can implement different functions, the device has more diverse functions compared with the device for verification that may implement only a single function in the related art. In a case where the apparatus for verification includes the first verification phantom and the third verification phantom, which can implement the same function, the device is more reliable in in verifying the deviation. Moreover, the device for verifying the radiotherapy system can be used in advance to verify the deviation between the isocenter of treatment and the isocenter of mechanical rotation, or to verify the deviation of the isocenter of mechanical rotation, to detect whether a deviation occurs to the position of the laser light, to verify an installation error of the image capture component and to verify the accuracy in image-guided positioning, in this way, a patient can be accurately positioned based on verification results during the radiotherapy, thereby improving the reliability of radiotherapy.

In addition, the first verification phantom 10 is provided with the slot 101 for holding the film, therefore, the film only need to be inserted in the slot 101 when the first verification phantom 10 is used to verify the deviation between the isocenter of treatment and the isocenter of mechanical rotation. Compared with the related art where the film need to be first inserted into a film cassette and then the film cassette with the film inserted is placed into a verification phantom, the device for verifying the radiotherapy system according to the present disclosure is more convenient to operate. Moreover, the film cassette with the film inserted needs to be extracted from the verification phantom multiple times in the related art, therefore, abrasions may be present between the film cassette and the verification phantom after long-term use, which can affect the accuracy in detecting the deviation of the isocenter of treatment. Therefore, the device for verifying the radiotherapy system according to the present disclosure is more reliable. Moreover, by integrating a plurality of functions into the second verification phantom 20, the production cost can also be saved on the premise of enriching the functions of the device for verifying the radiotherapy system.

It should be noted here that, in addition to at least two of the first verification phantom, the second verification phantom and the third verification phantom as described above, the device for verifying the radiotherapy system according to the embodiments of the present disclosure may also include other verification phantoms, which may be either verification phantoms identical to the first verification phantom, the second verification phantom and the third verification phantom as described above, or other types of verification phantoms.

In summary, according to the device for verifying the radiotherapy system provided by the embodiments of the present disclosure, as including at least two of a first verification phantom, a second verification phantom, and a third verification phantom that can fulfill different functions, the device can fulfill many functions. Compared with the device for verification that can only implement a single function in the related art, the device according to the present disclosure has more diverse functions.

Optionally, in an embodiment of the present disclosure, the radiotherapy system may include: a control host, an image server, an image capture component, a laser light, a radiation source, a treatment couch, and a scanner. The control host may include an upper computer and a lower computer. The image capture component may include a bulb tube and a detector disposed opposite to the bulb tube, and may also include a detector disposed opposite to the radiation source. It goes without saying that the detector disposed opposite to the bulb tube and the detector disposed opposite to the radiation source may be the same detector. The image server may also be connected to the control host or the image server may be directly integrated in the control host. The laser light may be a cross-hair laser light (that is, rays emitted by said laser light are cross-shaped rays).

The radiation source may emit rays (such as γ-rays or X-rays) to the first verification phantom 10 and the third verification phantom 30, and the bulb tube included in the image capture component may emit rays to the second verification phantom 20. After the radiation source emits rays to the first verification phantom 10, a therapist may take out the film from the first verification phantom 10, and scan the irradiated film through the scanner, so as to develop a focal spot formed on the film. Then, the therapist may upload images containing the focal spot to the image server. After the radiation source emits rays to the third verification phantom 30, the detector disposed opposite to the radiation source may receive the rays emitted by the radiation source, and then capture an image based on the rays. After the bulb tube emits rays to the second verification phantom 20, the detector disposed opposite to the bulb tube may receive the rays emitted by the radiation source, and then capture an image based on the rays. Afterwards, the detector may send the captured images to the image server. The image server may analyze the acquired images (such as to determine coordinates of a center point of each of the received images, and to determine a deviation between the isocenter of treatment and the isocenter of mechanical rotation), and then send an analysis result to the control host. Furthermore, the control host may directly adjust the position of the treatment couch based on the analysis result (such as the deviation).

Figure 2:
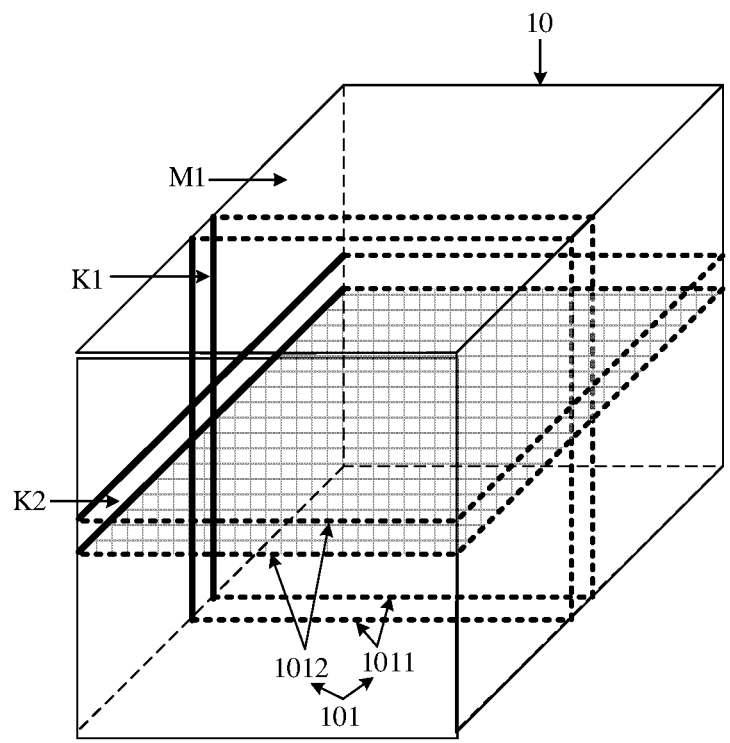
FIG. 2 is a schematic structural diagram of a first verification phantom in a device for verifying a radiotherapy system according to an embodiment of the present disclosure.

Optionally, FIG. 2 is a schematic structural diagram of a first verification phantom in a device for verifying a radiotherapy system according to an embodiment of the present disclosure. As illustrated in FIG. 2, the slots 101 of the first verification phantom 10 includes: a first slot 1011 and a second slot 1012. An insertion surface of the first slot 1101 is perpendicular to an insertion surface of the second slot 1012, and a center point of the insertion surface of the first slot 1011 and a center point of the insertion surface of the second slot 1012 are both in coincidence with the center point of the first verification phantom 10.

In a case where the first verification phantom 10 is configured to verify the deviation between the isocenter of treatment and the isocenter of mechanical rotation, a film is first inserted into the first slot 1011, and a center of the first verification phantom 10 is aligned with a mechanical isocenter; then, the radiation source (an initial rotation angle of a gantry may be 0 degree) irradiates the first verification phantom 10, thereby forming a focal spot on the film inserted in the first slot 1011; a therapist takes out the film inserted in the first slot 1011, and then inserts another film into the second slot 1012; the radiation source (the rotation angle of the gantry may be 90 degrees) irradiates the first verification phantom 10, thereby forming a focal spot on the film inserted in the second slot 1012; and the therapist may take out the film inserted in the second slot 1011. The two films are scanned by the scanner to obtain two images containing focal spots. Afterwards, the therapist may also upload the two images containing the focal spots to the image server. Since the beam focus of the radiation source theoretically is in coincidence with the mechanical isocenter, the image server may analyze the two images containing the focal spots to obtain actual coordinates of the beam focus, and then determine a deviation of the isocenter of treatment from the isocenter of mechanical rotation based on the actual coordinates of the beam focus and coordinates of the mechanical isocenter. Afterwards, the image server may send the deviation to the control host, such that the control host adjusts the position of the treatment couch based on the deviation. In addition, the control host may also store the deviation, and accurately position a patient based on the deviation during the radiotherapy.

Optionally, referring to FIG. 2, an opening K1 of the first slot 1011 and an opening K2 of the second slot 1012 may be both disposed on a first outer surface M1 of the first verification phantom 10.

The insertion and extraction of the films are facilitated by arranging the openings of the two slots on the same outer surface.

Figure 3:
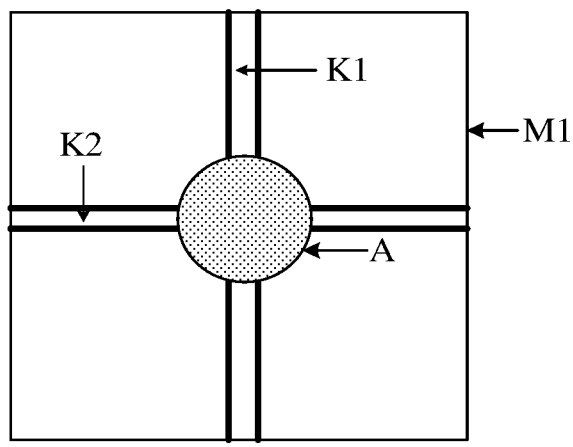
FIG. 3 is a side view of a first verification phantom in a device for verifying a radiotherapy system according to an embodiment of the present disclosure.

Optionally, referring to FIG. 3, an extraction groove A may be provided at a junction, on the first outer surface M1, of the opening K1 of the first slot 1011 and the opening K2 of the second slot 1012.

In an embodiment of the present disclosure, the extraction groove A is a groove recessed near an intersection point of the two slots. Moreover, the extraction groove A is in communication with both the first slot 1011 and the second slot 1012. The therapist may insert a film in or extract a film from the extraction groove. The therapist is better facilitated in inserting and extracting the film by arranging the extraction grooves A, respectively connected with the two slots, on the first outer surface M1.

Optionally, referring to FIG. 3, a cross section of the extraction groove A is circular. Alternatively, the cross section of the extraction groove A may be other shapes, such as a rectangle or a triangle. The cross section is a plane parallel to the first outer surface M1.

Optionally, the extraction groove A is disposed, on the first outer surface M1, at an intersection point of the first slot 1011 and the second slot 1012. For example, in a case where the intersection point of the first slot 1011 and the second slot 1012 is disposed at a center of the first outer surface M1, the extraction groove A is disposed at the center of the first outer surface M1.

Optionally, films inserted in the slots may be self-developing films. The size of a film inserted in each slot is matched with the size of the slot without shaking. That is, the size of a film inserted into the first slot 1011 is matched with the size of the first slot 1011, and the size of a film inserted into the second slot 1012 is matched with the size of the second slot 1012. Alternatively, the shape of the film may be also matched with an overall shape formed by the first slot 1011 and the second slot 1012. For example, the film may be a film composed of two sub-films that are perpendicular to and intersected with each other.

In an embodiment of the present disclosure, before a film is inserted into each slot, the film is cut into a size matched with the slot. By configuring the size of the film to match the size of each slot, the film inserted into the slot can be ensured to be shakeless, thereby improving the reliability in verifying the deviation between the isocenter of treatment and the isocenter of mechanical rotation.

Figure 4:
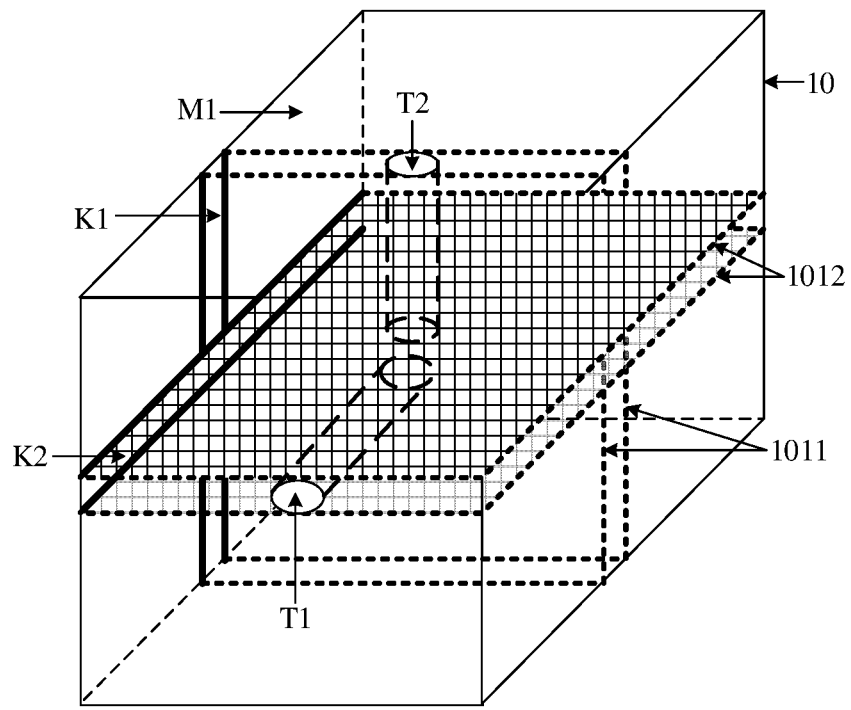
FIG. 4 is a schematic structural diagram of a second verification phantom in a device for verifying a radiotherapy system according to an embodiment of the present disclosure.

FIG. 4 is another schematic structural diagram of the first verification phantom 10 in the device for verifying the radiotherapy system according to an embodiment of the present disclosure. As illustrated in FIG. 4, the first verification phantom 10 is further provided with a first through hole T1 for communicating an outer surface of the first verification phantom 10 with the first slot 1011, and a second through hole T2 for communicating the outer surface of the first verification phantom 10 with the second slot 1012.

An extending direction of the first through hole T1 intersects with the insertion surface of the first slot 1011, and an intersection point of the first through hole T1 and the insertion surface of the first slot 1011 is the center point of the insertion surface of the first slot 1011. An extending direction of the second through hole T2 intersects with the insertion surface of the second slot 1012, and an intersection point of the second through hole T2 with the insertion surface of the second slot 1012 is the center point of the insertion surface of the second slot 1012.

As an example, referring to FIG. 4, the first verification phantom 10 is provided with the first through hole T1 at a side surface, and a second through hole T2 at a top surface. An extending direction of the first through hole T1 is perpendicular to an insertion surface of the first slot 1011; and an extending direction of the second through hole T2 is perpendicular to an insertion surface of the second slot 1012.

By the provision of the first through hole T1 and the second through hole T2, a needle or a colored pen core may be used first during deviation verification to pass through the first through hole T1 and make a mark at a center of a film inserted in the first slot 1011, and to pass through the second through hole T2 and make a mark at a center of a film inserted in the second slot 1012. Then, the two films are irradiated by the radiation source in the image capture component to form focal spots which are then analyzed by the scanner to obtain images with the focal spots. Here, since the center point of the first verification phantom 10 theoretically is in coincidence with the isocenter of mechanical rotation, the marks may be used as marks of the mechanical isocenter. Furthermore, it is convenient for the control host to subsequently determine a deviation between the mechanical isocenter and the isocenter of treatment, thereby improving the accuracy and efficiency in determining the deviation.

Optionally, the first verification phantom 10 may be a solid structure, and as illustrated in FIGS. 1, 2 and 4, the shape of the first verification phantom 10 may be cubic. Alternatively, the first verification phantom 10 may also have a structure of other shapes. For example, the first verification phantom 10 may be a prism. The shape of the first verification phantom 10 is not limited in the embodiments of the present disclosure.

Figure 5:
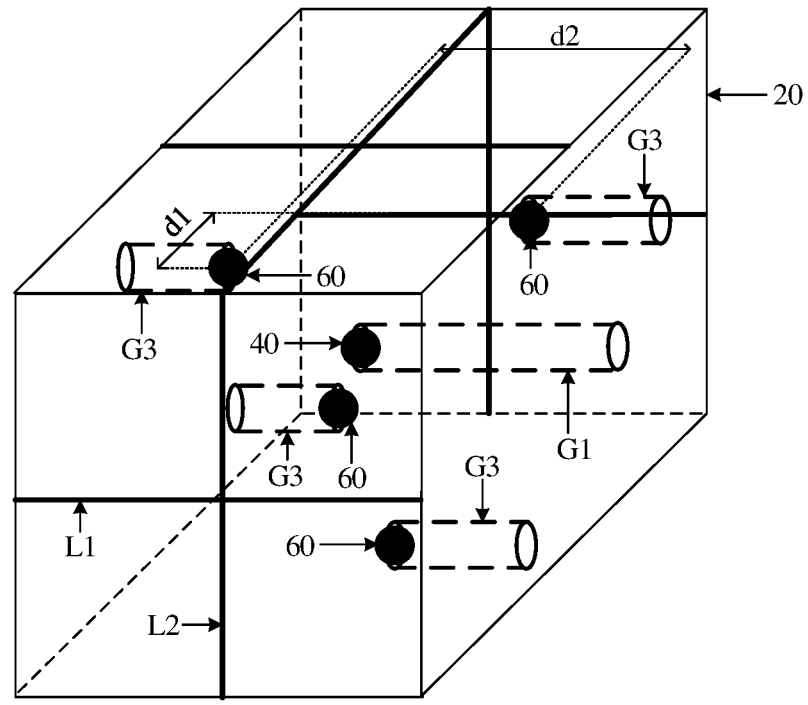
FIG. 5 is a schematic structural diagram of a second verification phantom in a device for verifying a radiotherapy system according to another embodiment of the present disclosure.

FIG. 5 is a schematic structural diagram of a second verification phantom 20 in the device for verifying the radiotherapy system according to an embodiment of the present disclosure. As illustrated in FIG. 5, an outer surface of the second verification phantom 20 may be provided with at least three sets of calibration lines (for example, FIG. 5 only illustrates three sets of calibration lines), and each set of calibration lines includes two calibration lines L1 and L2 perpendicular to each other. Assuming that an intersection point of the two calibration lines L1 and L2 included in each set of calibration lines is a target point, referring to FIG. 5, it can be seen that the respective target points among the at least three sets of calibration lines may be coplanar.

Among the at least three sets of calibration lines, two sets of the calibration lines are respectively disposed on two opposite side faces of the second verification phantom 20, and one set of the calibration lines is disposed at a surface, distal from a support that is configured to support the second verification phantom 20, of the second verification phantom 20. The support may be a treatment couch or a base.

As an example, assuming that the second verification phantom 20 is a rectangular parallelepiped as illustrated in FIGS. 1 and 5, referring to FIG. 5, it can be seen that a top surface and two opposite side surfaces of the second verification phantom 20 are respectively provided with two calibration lines L1 and L2 perpendicular to each other.

Due to installation errors or long-term use, a deviation may occur to the isocenter of mechanical rotation. Therefore, the radiotherapy system may verify the deviation of the isocenter of mechanical rotation by using the second verification phantom 20.

Optionally, in a case where the second verification phantom 20 is configured to verify the deviation of the isocenter of mechanical rotation, the device for verifying the radiotherapy system may be first placed on the treatment couch, in such a way that the two calibration lines L1 and L2, perpendicular to each other, disposed on each outer surface of the second verification phantom 20 are in coincidence with cross rays emitted from a laser light. Then, the control host may adjust a position of the treatment couch, such that a first positioning member 40 inside the second verification phantom 20 is aligned with the isocenter of mechanical rotation. Here, the bulb tube may irradiate the second verification phantom 20 at least twice at different angles. Accordingly, a detector installed opposite to the bulb tube may receive rays emitted from the radiation source, and capture at least two images of the first positioning member 40 based on the rays. Then, the detector may send the at least two generated images to the image server. Then, the image server may analyze the at least two images to determine the deviation of the isocenter of mechanical rotation, and send the determined deviation to the control host, such that the control host may accurately adjust the position of the treatment couch based on the deviation, thereby avoiding the effect of the deviation on the accuracy of radiotherapy. Moreover, the control host may also store the determined deviation, such that the control host may accurately position a patient based on the deviation during the radiotherapy.

Optionally, the control host may also pre-store relative positions (i.e., coordinates of positions where the first verification phantom 10 and the second verification phantom 20 are located) of the center point of the first verification phantom 10 and the center point of the first positioning member 40, therein. After the control host aligns the first positioning member 40 with the isocenter of mechanical rotation based on the deviation, the position of the treatment couch may be adjusted based on the pre-stored relative positions, such that the center point of the first verification phantom 10 is aligned with the isocenter of mechanical rotation.

Optionally, in an embodiment of the present disclosure two calibration lines L1 and L2 perpendicular to each other may be engraved on the outer surfaces (such as a top surface and two opposite side surfaces) of the second verification phantom 20. Alternatively, two calibration lines L1 and L2 perpendicular to each other may be also printed on the outer surfaces of the second verification phantom 20. Alternatively, two lines perpendicular to each other may be also attached to the outer surface of the second verification phantom 20, as the calibration lines L1 and L2.

In an embodiment of the present disclosure, the radiotherapy system may include three laser lights, with each laser light capable of emitting cross-shaped rays. One of the laser lights may be disposed opposite to a rotating gantry (for example, on a wall opposite to the rotating gantry) at a height higher than the height of the rotating gantry, and the laser light may be configured to verify whether a patient is lying straight on the treatment couch. The remaining two laser lights may be disposed on left and right sides of the rotating gantry (for example, on walls on the left and right sides) respectively; each of the remaining two laser lights may emit vertical-axis rays and horizontal-axis rays; and the vertical-axis and horizontal-axis rays emitted from each laser light may be perpendicular to each other (i.e., intersected to form cross-shaped rays).

Intersection points of the cross-shaped rays emitted from the three laser lights are reference points for positioning a patient, i.e., reference coordinates for positioning the phantoms. Therefore, by the provision of two calibration lines L1 and L2 perpendicular to each other on the top surface and two opposite side surfaces of the second verification phantom 20, whether the rays emitted from each laser light are perpendicular to each other can be detected, thereby detecting whether a deviation occurs to the position of the laser light. When a deviation is detected to occur to the position of a laser light, the position of the laser light may be adjusted in time based on the deviation, which further ensures the reliability of radiotherapy.

Optionally, as illustrated in FIG. 5, a plurality of third positioning members 60 are further disposed within the second verification phantom 20. Moreover, the plurality of third positioning members 60 are non-coplanar, and a number of the third positioning members 60 is not less than 4 (FIG. 5 illustrates four third positioning members 60).

The second verification phantom 20 may be further internally provided with a plurality of third positioning member pipes G3 corresponding to the plurality of third positioning members 60 one to one. Each third positioning member 60 is disposed in one corresponding third positioning member pipe G3.

As an example, referring to FIG. 5, the second verification phantom 20 is internally provided with four third positioning member pipes G3, and each of the four third positioning members 60 is disposed in one third positioning member pipe G3. Optionally, as illustrated in FIGS. 1 and 5, the second verification phantom 20 may be further internally provided with a first positioning member pipe G3, in which the first positioning member 40 may be disposed.

Optionally, as illustrated in FIGS. 1 and 5, the first positioning member 40 and the third positioning members 60 may be both spherical in shape, therefore, the first positioning member 40 may be also referred to as a first positioning ball, and the third positioning members 60 may be also referred to as third positioning balls. Accordingly, the first positioning member 40 and the third positioning members 60 may be both 6 mm in diameter. Distances between any two of the third positioning members are equal. That is, for any two of the plurality of third positioning members 60, an interval between the two third positioning members 60 in a first direction and an interval between the two third positioning members 60 in a second direction may be both 60 mm. The first direction is perpendicular to the second direction. Distances between each of the plurality of third positioning members 60 and the first positioning member 40 may be $30\sqrt{3}$ mm (approximately 51.96 mm).

As an example, assuming that the second verification phantom 20 is a cube as illustrated in FIGS. 1 and 5, the first direction may be a length direction of the second verification phantom 20, and the second direction may be a width direction of the second verification phantom 20; or, the first direction may be the length direction of the second verification phantom 20, and the second direction may be a height direction of the second verification phantom 20; or, the first direction may be the width direction of the second verification phantom 20, and the second direction may be the height direction of the second verification phantom 20. Referring to FIG. 5, it can be seen that an interval d1 between two of the third positioning members 60 in the width direction of the second verification phantom 20 is 60 mm, and an interval d2 between two of the third positioning members 60 in the length direction of the second verification phantom 20 is also 60 mm.

In an embodiment of the present disclosure, when the first positioning member 40 and the plurality of third positioning members 60 satisfy the above geometric relationship, the second verification phantom 20 may be also used as a geometric calibration phantom. That is, the second verification phantom 20 may be configured to detect geometric calibration parameters, for example, an installation error of the image capture component (i.e., the detector or the ball tube), in the radiotherapy system. Moreover, the second verification phantom 20 may also be configured to verify the accuracy in image-guided positioning.

As an example, the first positioning member 40 may be configured to simulate a target point at an affected part of a patient, and the plurality of third positioning members 60 may be configured to simulate reference points around the target point. Errors may occur when a therapist positions the patient. Therefore, in order to verify the accuracy in correcting the image-guided positioning, images may be acquired by performing image capture on the first positioning member 40 and the plurality of third positioning members 60 with the image capture component; and whether the position of the target point (or a position of a point other than the target point) and an actual position of the target point meet the requirements of relevant standards may be determined based on a CT scheme of the second verification phantom 20.

Optionally, in order to prevent materials of the positioning balls from unnecessarily affecting the radiotherapy, when the second verification phantom 20 is used for performing CT scanning and making a treatment scheme, the density of the materials selected for the first positioning member 40 and the plurality of third positioning members 60 may be similar to the bone density of a human body. For example, the first positioning member 40 and the plurality of third positioning members 60 may be both made of at least one of aluminum, Teflon, glass or ceramic. This is not limited in the embodiments of the present disclosure.

Optionally, the second verification phantom 20 may also have a solid structure. Referring to FIG. 1 and FIG. 5, it can be seen that the shape of the second verification phantom 20 may be a rectangular parallelepiped.

Figure 6:
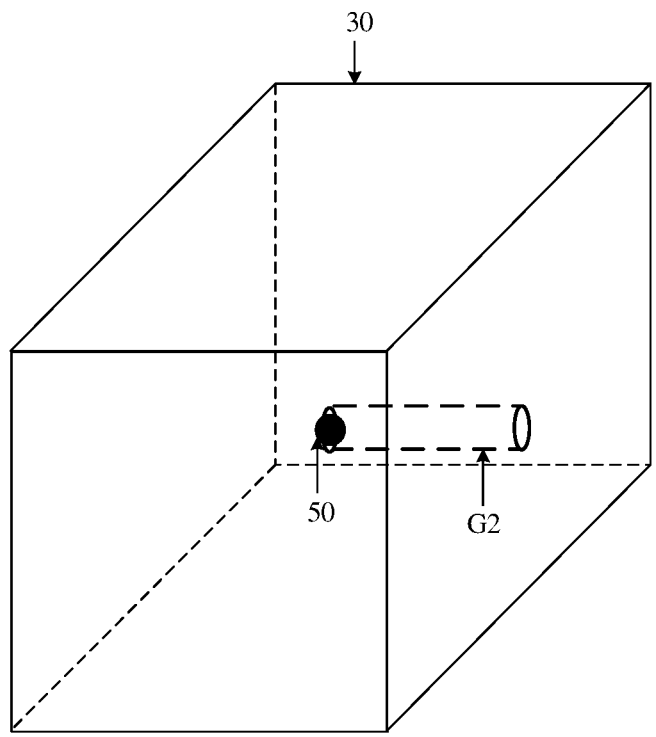
FIG. 6 is a schematic structural diagram of a third verification phantom in a device for verifying a radiotherapy system according to an embodiment of the present disclosure.

FIG. 6 is a schematic structural diagram of a third verification phantom 30 in the device for verifying the radiotherapy system according to an embodiment of the present disclosure. As illustrated in FIG. 6, the third verification phantom 30 may be an internally hollow housing.

Accordingly, referring to FIGS. 1 and 6, a second positioning member pipe G2 may be disposed inside the housing, so as to allow the second positioning member 50 to be located at the center of the third verification phantom 30. Here, the second positioning member 50 may be disposed in the second positioning member pipe G2. Optionally, the first positioning member pipe G1, the second positioning member pipe G2, and the third positioning member pipe G3 may be all referred to as fixed-position measuring sticks.

Optionally, in a case where the third verification phantom 30 is configured to verify a deviation between the isocenter of treatment and the isocenter of mechanical rotation, the third verification phantom 30 may be irradiated at least twice at different angles by using the radiation source; and the detector installed opposite to the radiation source may receive the rays emitted from the radiation source, and capture at least two images based on the received rays. Then, the detector may send the at least two generated images to the image server. The at least two images are then analyzed by the image server to obtain coordinates of center points in the at least two images (i.e., the coordinates of the second positioning member 50). Then, the image server may determine, based on the coordinates of the second positioning member 50, actual coordinates of a beam focus, and further determine a deviation of the isocenter of treatment from the isocenter of mechanical rotation. Moreover, the image server may also send the deviation to the control host, which then adjusts the position of the treatment couch based on the deviation. In addition, the control host may also store the deviation.

By designing the third verification phantom 30 as an internally hollow housing, it is possible to avoid the problem that in a case where the respective outer surfaces of the third verification phantom 30 are different in thickness, attenuation occurs to different extents when the rays emitted from the radiation source at different angles irradiate the second positioning member 50 for imaging. Furthermore, it is possible to avoid the difficulty in later image analysis caused by nonuniform brightness of a light spot generated on the second positioning member 50 during imaging.

Optionally, the second positioning member 50 is made of tungsten; the second positioning member 50 may be a sphere, and thus may also be called a tungsten bead; and the diameter of the second positioning member may be 7 mm. Moreover, referring to FIG. 1 and FIG. 6, it can be seen that the shape of the third verification phantom 30 may be a rectangular parallelepiped. Alternatively, the third verification phantom 30 may also have a structure of other shapes. For example, for the sake of structural aesthetics, the third verification phantom 30 may be a hemisphere. This is not limited in the embodiments of the present disclosure.

Figure 7:
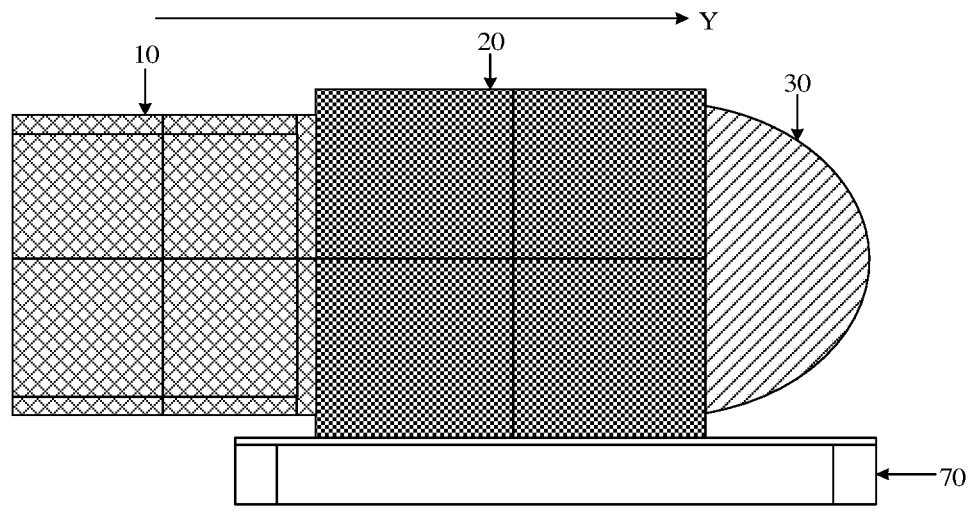
FIG. 7 is a side view of a device for verifying the radiotherapy system according to an embodiment of the present disclosure.

FIG. 7 is a side view of a device for verifying a radiotherapy system according to an embodiment of the present disclosure. As illustrated in FIG. 7, the device for verifying the radiotherapy system includes: a first verification phantom 10, a second verification phantom 20 and a third verification phantom 30. The first verification phantom 10, the second verification phantom 20, and the third verification phantom 30 may be sequentially arranged along a length direction Y of a treatment couch.

Figure 8:
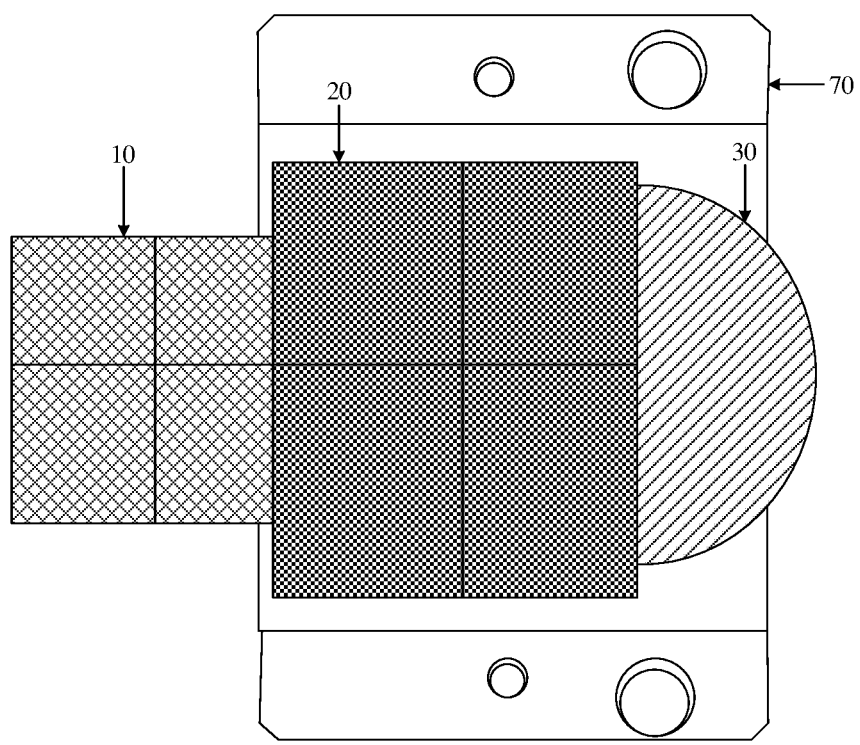
FIG. 8 is a top view of a device for verifying the radiotherapy system according to an embodiment of the present disclosure.
Figure 9:
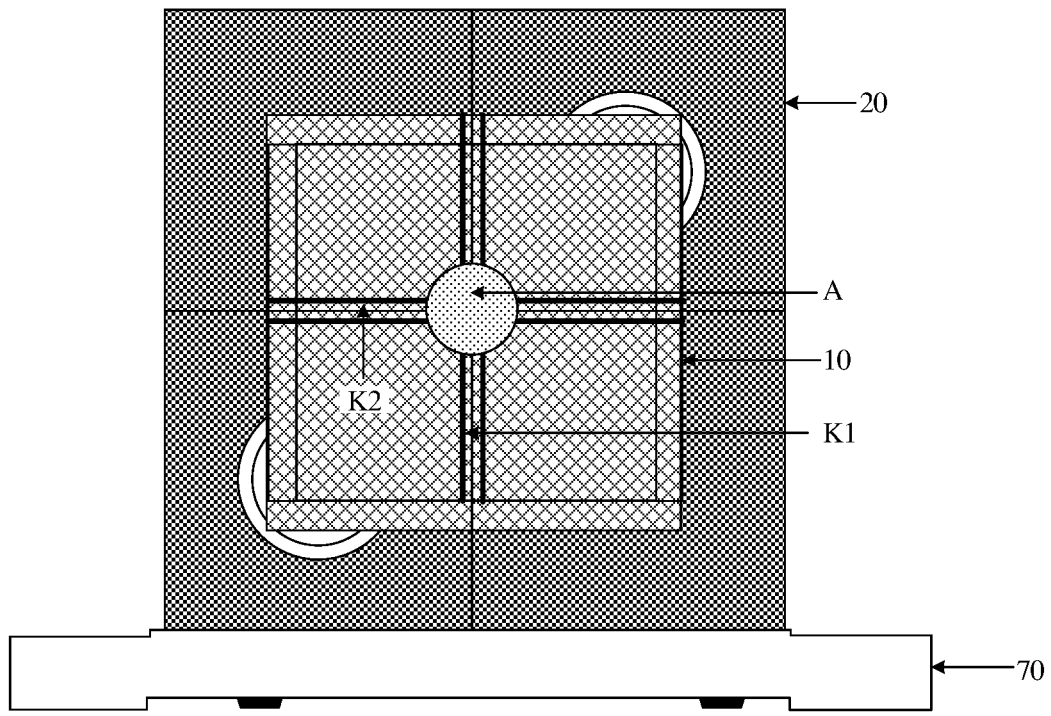
FIG. 9 is a left side view of a device for verifying the radiotherapy system according to an embodiment of the present disclosure.

FIG. 8 is a top view of a device for verifying a radiotherapy system according to an embodiment of the present disclosure. FIG. 9 is a left side view of a device for verifying the radiotherapy system according to an embodiment of the present disclosure. Referring to FIGS. 7 to 8, it can be seen that, in an embodiment of the present disclosure, the first verification phantom 10, the second verification phantom 20 and the third verification phantom 30 may be connected in sequence along a length direction of the treatment couch. The first verification phantom 10 may be a cube, the second verification phantom 20 may be a rectangular parallelepiped, and the third verification phantom 30 may be a hemisphere. Moreover, referring to FIG. 9, it can be seen that an opening K1 of the first slot and an opening K2 of the second slot of the first verification phantom 10 are both disposed on the same outer surface, on which an extraction groove A in communication with both the first slot and the second slot is further disposed.

Optionally, a pasting tool (such as a medical adhesive) may be used to paste the first verification phantom 10, the second verification phantom 20 and the third verification phantom 30 in sequence, and accordingly, a distance between the first verification phantom 10 and the second verification phantom 20 and a distance between the second verification phantom 20 and the third verification phantom 30 are both 0. Alternatively, a connecting component (such as a connecting rod) may be used to connect the first verification phantom 10, the second verification phantom 20 and the third verification phantom 30 in sequence, and accordingly, a distance between the first verification phantom 10 and the second verification phantom 20 and a distance between the second verification phantom 20 and the third verification phantom 30 may be or may not be 0. This is not limited in the embodiments of the present disclosure.

In addition, in a case where the device for verifying the radiotherapy system includes the third verification phantom 30, the second positioning member 50 made of a metal material is disposed at the center of the third verification phantom 30. Therefore, in order to prevent the second positioning member 50 from affecting a verification result in a case where the third verification phantom 30 is configured to verify the deviation between the isocenter of treatment and the isocenter of mechanical rotation under nuclear-magnetic resonance scanning, third verification phantom 30 may be detachably connected with the first verification phantom 10 or the second verification phantom 20. That is, the third verification phantom 30 is detachable.

Optionally, in an embodiment of the present disclosure, referring to FIGS. 7 to 9, the device for verifying the radiotherapy system may further include a base 70, on which at least one of the first verification phantom 10, the second verification phantom 20, or the third verification phantom 30 may be disposed. The base 70 may be disposed on the treatment couch.

Optionally, the first verification phantom 10, the second verification phantom 20, and the third verification phantom 30 may be connected in sequence and then fixed on the base 70 by fixing parts (such as screws); or, the first verification phantom 10, the second verification phantom 20, and the third verification phantom 30 may also be connected in sequence and then directly placed on the treatment couch without a base. This is not limited in the embodiments of the present disclosure.

In an embodiment of the present disclosure, by sequentially connecting the first verification phantom 10, the second verification phantom 20, and the third verification phantom 30, which have different functions, to form a device for verifying the radiotherapy system, the device according to the embodiments of the present disclosure has more diverse functions, as compared with the device for verification that may only implement a single function in the related art.

Optionally, in an embodiment of the present disclosure, housings of the first verification phantom 10, the second verification phantom 20, and the third verification phantom 30 may be all made of organic glass. Since the organic glass is inferior in blocking rays, that is, the attenuation of the rays passing through the organic glass is small, the reliability in detecting the deviation between the isocenter of treatment and the isocenter of mechanical rotation is ensured. Moreover, the cost of the organic glass is also low.

In summary, according to the device for verifying the radiotherapy system provided by the embodiments of the present disclosure, as including at least two of a first verification phantom, a second verification phantom, and a third verification phantom that can fulfill different functions, the device can fulfill many functions. Compared with the device for verification that can only implement a single function in the related art, the device according to the present disclosure has more diverse functions.

An embodiment of the present disclosure further provides a radiotherapy system. The radiotherapy system may include: a device for verifying the radiotherapy system as illustrated in any one of FIGS. 1 to 9 and a radiotherapy device.

Optionally, the radiotherapy device may include: a radiation source and a treatment couch. Based on this, the radiotherapy device may further include: an image capture component, which includes a detector disposed opposite to the radiation source, and/or an imaging device (including a bulb tube and a flat panel detector disposed opposite to the bulb tube). The radiotherapy system may further include: a control host, an image server, a scanner and three laser lights.

The device for verifying the radiotherapy system may be disposed on the treatment couch; the image capture component may be connected to the image server; the image server may be connected to the control host; and the control host may be connected to the treatment couch. Alternatively, the image server may be also directly integrated in the control host. The radiation source may be a radiation source of a treatment head in the radiotherapy device, that is, rays emitted by the radiation source may be also configured to irradiate a target point on a patient, so as to perform radiotherapy on the patient.

In an embodiment of the present disclosure, the scanner may be configured to scan a film, irradiated by the radiation source, in the device for verifying the radiotherapy system to develop a focal spot formed on the film, and a therapist may send an image containing the focal spot to the image server. The image capture component and the radiation source may be configured to capture images of the device for verifying the radiotherapy system and send the captured images to the image server. The image server may be configured to analyze the acquired images and determine a deviation (such as a deviation between the isocenter of treatment and the isocenter of mechanical rotation) based on an analysis result; and the image server may further send the determined deviation to the control host. The control host may be configured to adjust the position of the treatment couch based on the received deviation, and may store the deviation. Each laser light may be configured to emit rays to the device for verifying the radiotherapy system. Optionally, the rays emitted from the laser light may be cross-shaped rays.

Optionally, the control host may include an upper computer and a lower computer; the upper computer may be connected to the lower computer; and the lower computer may be connected to other parts (such as the treatment couch and the image capture component) in the radiotherapy system. The upper computer may be configured to send a control instruction to the lower computer; and the lower computer may control working statuses of other parts based on the received control instruction.

In summary, the embodiments of the present disclosure provide a radiotherapy system which includes a device for verifying the radiotherapy system. The radiation source in the radiotherapy device and the bulb tube in the image capture component may emit rays to the device for verifying the radiotherapy system; the detector disposed opposite to the radiation source and the detector disposed opposite to the bulb tube may receive the rays and capture images based on the rays; and the detector may send the captured images to the image server. The scanner may scan a film, irradiated by the radiation source, in the device for verifying the radiotherapy system to develop a focal spot formed on the film, and a therapist may send an image containing the focal spot to the image server. The image server may analyze the acquired images to determine the deviation between the isocenter of treatment and the isocenter of mechanical rotation or to determine the deviation of the isocenter of mechanical rotation, and may send the deviation to the control host, which will accurately position the patient based on the deviation. As a result, the accuracy of radiotherapy is improved, and the quality of radiotherapy is guaranteed.

An embodiment of the present disclosure provides a method for verifying a radiotherapy system. The method may include: at least one of a first verification process, a second verification process, or a third verification process.

Figure 10:
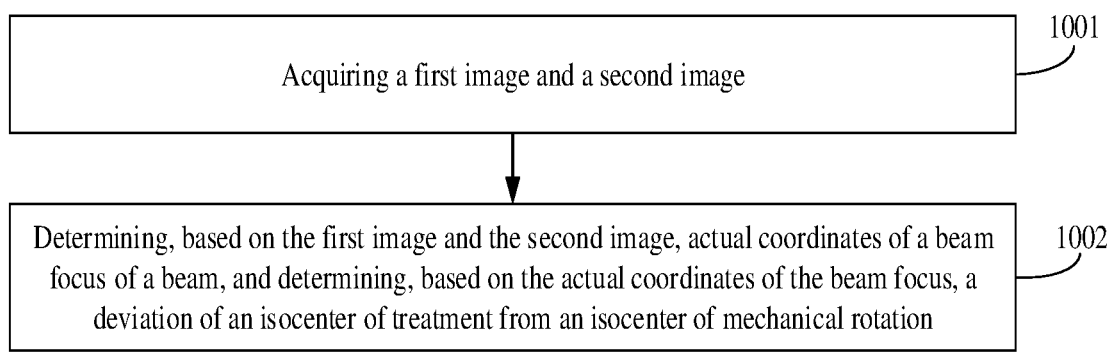
FIG. 10 is a flowchart of a method for a first verification process according to an embodiment of the present disclosure.

FIG. 10 is a flowchart of a method for a first verification process according to an embodiment of the present disclosure. As illustrated in FIG. 10, the first verification process may include the following steps.

In step 1001, a first image and a second image are acquired.

In an embodiment of the present disclosure, the first image and the second image may be obtained by respectively irradiating two films inserted in slots of a first verification phantom with a beam and then scanning the two irradiated films respectively. As an example, the first image may be obtained by irradiating a film inserted into a first slot of the first verification phantom with a beam from a radiation source, and then scanning the irradiated film. The second image may be acquired by irradiating a film inserted into a first slot of the second verification phantom with the beam from the radiation source, and then scanning the irradiated film.

As an example, the radiation source may emit rays to the device for verifying the radiotherapy system to, at this point, form a focal spot at a center of the film inserted in the first verification phantom. Then, a therapist may take out the films from the first verification phantom, and scan the films by a scanner, so as to develop focal spots formed on the films. Lastly, the therapist may also upload the first and second images containing the focal spots to the image server. That is, the image server may acquire the first image and the second image.

In addition, after the films are inserted in the slots, a needle or a colored pen core may be also first used to pass through the through hole for making marks at center positions of the two films. Here, since the center of the first verification phantom is aligned with the isocenter of mechanical rotation, the marks may be used as theoretical coordinates of the isocenter of mechanical rotation. Accordingly, the image server may be facilitated to determine the deviation between the isocenter of treatment and the isocenter of mechanical rotation based on these marks. That is, the accuracy and efficiency of determining the deviation between the isocenter of treatment and the isocenter of mechanical rotation may be improved.

In step 1002, actual coordinates of a beam focus of the beam are determined based on the first image and the second image, and a deviation of an isocenter of treatment from an isocenter of mechanical rotation is determined based on the actual coordinates of the beam focus.

An imaging point is a beam focus of the rays emitted from a radiation source. Therefore, the image server may also determine the actual coordinates of the beam focus of the beam based on the first image and the second image.

The coordinates of the focal spots in the first image and the second image are the coordinates in a two-dimensional image coordinate system. Therefore, the image server may perform coordinate transformation on the coordinates of the focal spot in the acquired first image and the coordinates of the focal spot in the second image, thereby obtaining the coordinates of the focal spots in a three-dimensional device coordinate system. The coordinates are the actual coordinates of the beam focus. Further, after acquiring the actual coordinates of the beam focus, the image server may also determine the deviation between the coordinates of the isocenter of treatment and the coordinates of the isocenter of mechanical rotation based on the actual coordinates of the beam focus (i.e., the actual coordinates of the isocenter of treatment). Then, the image server may send the determined deviation to the control host, such that the control host stores the determined deviation. Afterwards, during radiotherapy, the control host may accurately position the patient directly based on the deviation. Alternatively, the control host may adjust the position of the treatment couch directly based on the deviation after verifying the deviation, such that the center point of the first verification phantom is aligned with the beam focus.

Since the center point of the first verification phantom may be configured to simulate a target point of an affected part, the target point may be aligned with the actual beam focus after the position of the treatment couch is adjusted. The problem that the beam focus cannot accurately irradiate the target point due to the deviation of the isocenter of treatment caused by installation errors is solved, and the accuracy of radiotherapy is improved, thereby ensuring the quality of radiotherapy.

Figure 11:
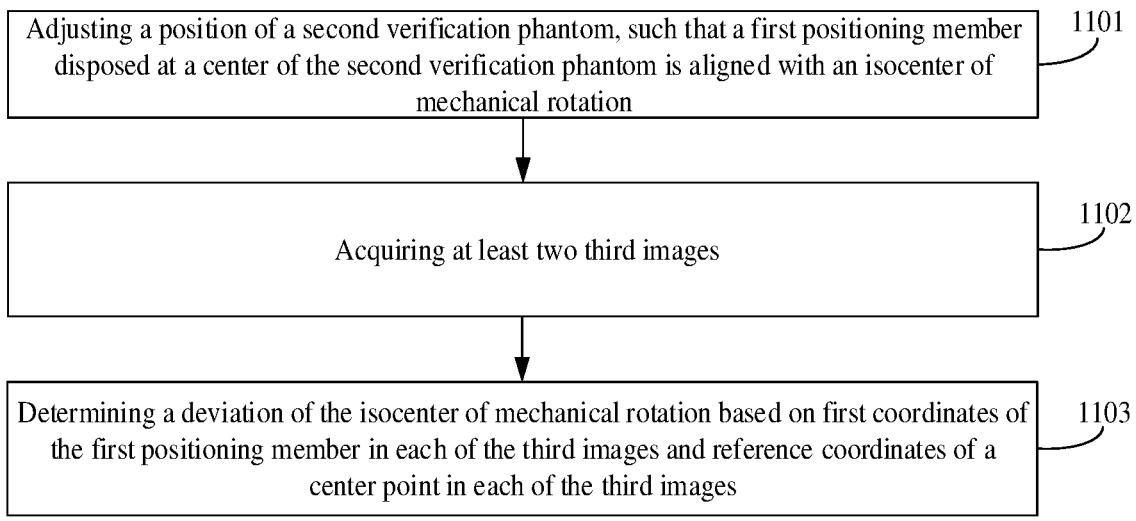
FIG. 11 is a flowchart of a method for a second verification process according to an embodiment of the present disclosure.

FIG. 11 is a flowchart of a method for a second verification process according to an embodiment of the present disclosure. As illustrated in FIG. 11, the second verification process may include the following steps.

In step 1101, a position of the second verification phantom is adjusted, such that a first positioning member disposed at a center of the second verification phantom is aligned with an isocenter of mechanical rotation.

In an embodiment of the present disclosure, rays emitted from a laser light may be cross-shaped rays. Theoretically, when the second verification phantom is placed on the treatment couch, an interaction point of the cross-shaped rays emitted from the laser light is reference coordinates for phantom positioning. Further, when two calibration lines disposed on each outer surface of the second verification phantom coincidence with the cross-shaped rays emitted from the laser light, the position of the treatment couch may be first adjusted first, and the second verification phantom may be moved to a treatment space, such that the first positioning member disposed inside the second verification phantom is aligned with the isocenter of the mechanical rotation. Here, the center point (i.e., the first positioning member) of the second verification phantom is theoretical coordinates of the isocenter of the mechanical rotation.

Optionally, the control host may be connected to the treatment couch, and the therapist may first place the device for verifying the radiotherapy system on the upper couch position of the treatment couch. Then, the control host may adjust the position of the treatment couch, such that each calibration line disposed on each outer surface of the second verification phantom is in coincidence with the rays emitted from the laser light. Alternatively, the therapist may directly adjust the position of the second verification phantom, such that each calibration line disposed on each outer surface of the second verification phantom is in coincidence with the rays emitted from the laser light. Then, the control host may continue to adjust the position of the treatment couch, such that the center point of the second verification phantom is aligned with the isocenter of mechanical rotation.

In step 1102, at least two third images are acquired.

In an embodiment of the present disclosure, after the second verification phantom is moved to such an extent that its center point is aligned with the coordinates of a mechanical isocenter, the image server may acquire at least two third images. Each of the third images may be an image acquired by performing image capture on the first positioning member in the second verification phantom by the image capture component.

Optionally, the bulb tube in the image capture component may emit X-rays to the second verification phantom. Here, a detector disposed opposite to the bulb tube may receive the X-rays, thereby implementing the image capture for the first positioning member. Further, the detector may send the captured third images to the image server. Accordingly, the image server may acquire at least two third images.

In step 1103, a deviation of the isocenter of mechanical rotation is determined based on first coordinates of the first positioning member in each of the third images and reference coordinates of a center point in each of the third images.

When the image server acquires at least two third images, first coordinates of the first positioning member in each of the third images and reference coordinates of a center point in each of the third images may be further acquired. Then, the image server may also determine the deviation of the isocenter of mechanical rotation based on the acquired first coordinates and reference coordinates. Here, since the center point of the second verification phantom is theoretically aligned with the isocenter of mechanical rotation, the image server may determine the reference coordinates of the center point of the acquired third image as the theoretical coordinates of the isocenter of mechanical rotation. The first coordinates of the first positioning member are the actual coordinates of the isocenter of the mechanical rotation. The above-mentioned theoretical coordinates and actual coordinates are both coordinates in the two-dimensional image coordinate system.

Further, the image server may also perform coordinate transformation on the at least two acquired first coordinates to obtain the actual coordinates of the isocenter of mechanical rotation in the three-dimensional device coordinate system, and may perform coordinate transformation on the at least two acquired reference coordinates to obtain the theoretical coordinates of the isocenter of mechanical rotation in the three-dimensional device coordinate system. Then, the image server may calculate the deviation of the isocenter of mechanical rotation based on the determined actual coordinates and theoretical coordinates of the mechanical isocenter, and send the determined deviation to the control host. Optionally, the control host may further store the deviation of the isocenter of mechanical rotation, so that a patient can be accurately positioned directly based on the deviation during the radiotherapy.

Figure 12:
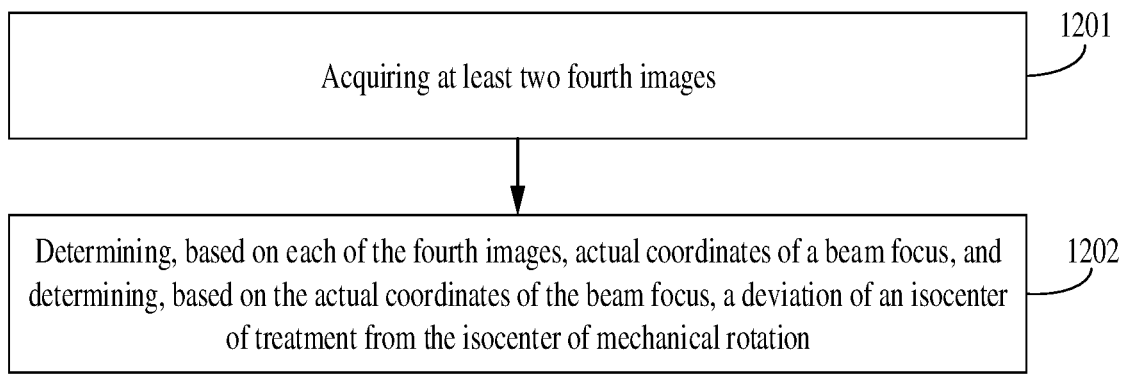
FIG. 12 is a flowchart of a method for a third verification process according to an embodiment of the present disclosure.

FIG. 12 is a flowchart of a method for a third verification process according to an embodiment of the present disclosure. As illustrated in FIG. 12, the method may include the following steps.

In step 1201, at least two fourth images are acquired.

The fourth images may be images that are obtained by irradiating the second positioning member with a beam by the radiation source in the image capture component and then performing image capture. Optionally, the radiation source in the image capture component may irradiate the third verification phantom at least twice. That is, the radiation source may emit rays to the third verification phantom at least twice. Accordingly, the detector disposed opposite to the radiation source may receive the rays and capture at least two fourth images based on the received rays. Moreover, the detector may send the at least two generated fourth images to the image server. That is, the image server may acquire the images captured by the image capture component.

In step 1202, actual coordinates of a beam focus are determined based on each of the fourth images as obtained, and a deviation of an isocenter of treatment from the isocenter of mechanical rotation is determined based on the actual coordinates of the beam focus.

An imaging point is a beam focus of the rays emitted from a radiation source. Therefore, after acquiring the at least two fourth images, the image server may also determine the actual coordinates of the beam focus based on each of the at least two images.

The image server may analyze each of the at least two acquired fourth images, to obtain coordinates of a center point in each fourth image. For example, the image server may acquire two images, and analyze the two fourth images to obtain the coordinates of the center point of each fourth image. Since the actual coordinates of the beam focus are coordinates in the three-dimensional device coordinate system, and the coordinates of the center point of each fourth image are coordinates in the two-dimensional image coordinate system, the image server, by acquiring at least two fourth images, may perform coordinate transformation on the coordinates of the center point of each of the at least two fourth images, to obtain coordinates of the center points of the fourth images in the three-dimensional device coordinate system. Accordingly, the image server may determine the coordinates of the center points of the fourth images in the three-dimensional device coordinate system as the actual coordinates of the beam focus.

Further, after acquiring the actual coordinates of the beam focus, the image server may also determine the deviation between the coordinates of the isocenter of treatment and the isocenter of mechanical rotation based on the actual coordinates of the beam focus (i.e., the actual coordinates of the isocenter of treatment). Then, the image server may send the determined deviation to the control host, which adjusts the position of the treatment couch based on the deviation, thereby aligning the center point of the third verification phantom with the beam focus. In addition, the control host may also store the determined deviation, and afterwards, the control host may accurately position a patient directly based on the deviation during the radiotherapy.

Since the center point of the third verification phantom may be configured to simulate a target point of an affected part, the target point may be aligned with the actual beam focus after the position of the treatment couch is adjusted. The problem that the beam focus cannot accurately irradiate the target point due to the deviation of the isocenter of treatment caused by installation errors is solved, and the accuracy of radiotherapy is improved, thereby ensuring the quality of radiotherapy.

In summary, according to the method for verifying the radiotherapy system provided by the embodiments of the present disclosure, at least one of a first verification process, a second verification process or a third verification process is included, that is, the radiotherapy system can fulfill at least one of the functions of verifying the deviation between the isocenter of treatment and the isocenter of mechanical rotation, or verifying the deviation of the isocenter of mechanical rotation, by using the device for verifying the radiotherapy system. Therefore, the method for verifying the radiotherapy system can fulfill more diverse functions.

Optionally, the method includes: a first verification process, a second verification process, and a third verification process. After the second verification process (i.e., step 1103 above) is executed, the radiotherapy system may also adjust the position of the treatment couch based on the deviation, such that a first positioning member inside the second verification phantom is aligned with the isocenter of mechanical rotation. For example, the control host may adjust the position of the treatment couch based on the received deviation, such that the first positioning member in the second verification phantom is aligned with the isocenter of mechanical rotation.

Further, the radiotherapy system may adjust the position of the treatment couch based on a relative position of the center point of the first verification phantom with respect to the first positioning member, such that the center point of the first verification phantom is aligned with the isocenter of mechanical rotation. Optionally, the control host may pre-store the relative position of the center point of the first verification phantom with respect to the first positioning member (that is, the control host may pre-store the coordinates of the first and second verification phantoms in the three-dimensional device coordinate system, therein). Accordingly, the control host may adjust the position of the treatment couch based on the relative position of the center point of the first verification phantom with respect to the first positioning member, such that the center point of the first verification phantom is aligned with the isocenter of the mechanical rotation.

In addition, after the center point of the first verification phantom is aligned with the isocenter of mechanical rotation, the imaging server in the radiotherapy system may also continue to verify whether a deviation exists between the isocenter of treatment and the isocenter of mechanical rotation by using the first verification phantom. That is, the above-mentioned first verification process (i.e., steps 1001 and 1002 above) may be executed continuously.

After executing the first verification process (i.e., step 1002 above), the radiotherapy system may also adjust the position of the treatment couch based on the relative position of the second positioning member with respect to the first positioning member, such that the second positioning member is aligned with the isocenter of mechanical rotation. Optionally, the control host may pre-store a relative position of the second positioning member disposed at the center of the third verification phantom with respect to the first positioning member (that is, the control host may also pre-store the coordinates of the third verification phantom in the three-dimensional device coordinate system). Accordingly, the control host may adjust the position of the treatment couch based on the relative position of the second positioning member with respect to the first positioning member, such that the second positioning member is aligned with the isocenter of the mechanical rotation.

In addition, after the second positioning member is aligned with the isocenter of mechanical rotation, the image server in the radiotherapy system may also continue to verify whether a deviation exists between the isocenter of treatment and the isocenter of mechanical rotation, by using the third verification phantom. That is, the third verification process (i.e., steps 1201 and 1202 above) may be executed continuously. That is, the radiotherapy system may sequentially execute the second verification process, the first verification process, and the third verification process.

Optionally, the control host may also pre-store a relative position of the second positioning member disposed inside the third verification phantom with respect to the center point of the first verification phantom (that is, the control host may pre-store the coordinates of the first and third verification phantoms in the three-dimensional device coordinate system). Accordingly, after the above third verification process (i.e., step 1202 above) is executed, the control host may also adjust the position of the treatment couch based on the relative position, such that the center point of the first verification phantom is aligned with the isocenter of mechanical rotation.

However, errors may also occur when the upper computer adjusts the position of the treatment couch. That is, even if the upper computer has adjusted the second positioning member to align with the actual beam focus, the beam focus may deviate again when the upper computer adjusts the position of the treatment couch again. That is, the center point of the first verification phantom may not be aligned with the actual beam focus. Here, in order to ensure the accuracy of radiotherapy, the image server and the control host in the radiotherapy system may continue to execute the first verification process, i.e., continuing to verify whether a deviation exists between the center point of the first verification phantom and the isocenter of mechanical rotation. Alternatively, after the first verification process is executed, the position of the treatment couch is adjusted based on the deviation between the actual coordinates of the beam focus and the coordinates of the isocenter of mechanical rotation, such that the control host may also adjust the position of the treatment couch based on said relative position after the center point of the first verification phantom is aligned with the beam focus, thereby aligning the second positioning member with the isocenter of mechanical rotation. Accordingly, the control host may also continue to execute the third verification process above, so as to further ensure that the second positioning member is aligned with the actual beam focus after the treatment couch is adjusted, and to improve the accuracy of radiotherapy. That is, the first verification process and the third verification process may mutually verify the deviation of the isocenter of treatment from the isocenter of mechanical rotation, thereby improving the reliability in determining the deviation.

In summary, according to the method for verifying the radiotherapy system provided by the embodiments of the present disclosure, at least one of a first verification process, a second verification process or a third verification process is included, that is, the radiotherapy system can fulfill at least one of the functions of verifying the deviation between the isocenter of treatment and the isocenter of mechanical rotation, or verifying the deviation of the isocenter of mechanical rotation, by using the device for verifying the radiotherapy system. Therefore, the method for verifying the radiotherapy system can fulfill more diverse functions.

An embodiment of the present disclosure provides an apparatus for verifying the radiotherapy system, which may include: at least one of a first verification module, a second verification module, or a third verification module. For example, the apparatus for verifying the radiotherapy system may include at least two verification modules.

Figure 13:
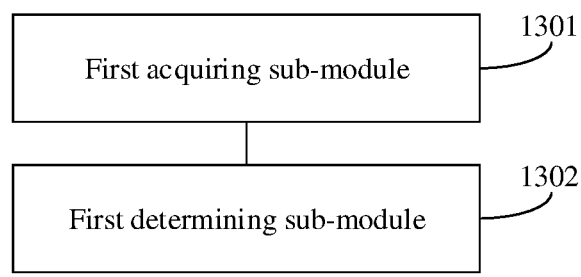
FIG. 13 is a block diagram of a first verification module in an apparatus for verifying a radiotherapy system according to an embodiment of the present disclosure.

FIG. 13 is a block diagram of a first verification module according to an embodiment of the present disclosure. As illustrated in FIG. 13, the first verification module may include the following sub-modules.

A first acquiring sub-module 1301 is configured to acquire a first image and a second image.

The first image and the second image may be obtained by respectively irradiating two films inserted in slots of a first verification phantom with a beam and then scanning the two irradiated films respectively.

A first determining sub-module 1302 is configured to determine, based on the first image and the second image, actual coordinates of a beam focus of a beam, and determine, based on the actual coordinates of the beam focus, a deviation of an isocenter of treatment from an isocenter of mechanical rotation.

Figure 14:
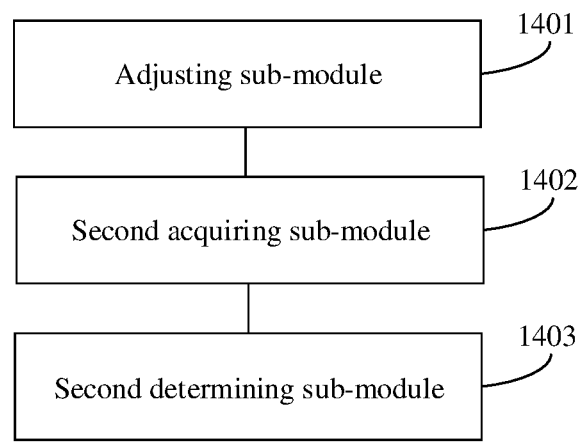
FIG. 14 is a block diagram of a second verification module in the apparatus for verifying the radiotherapy system according to an embodiment of the present disclosure.

FIG. 14 is a block diagram of a second verification module according to an embodiment of the present disclosure. As illustrated in FIG. 14, the second verification module may include the following sub-modules.

An adjusting sub-module 1401 is configured to adjust a position of a second verification phantom, such that a first positioning member disposed at a center of the second verification phantom is aligned with an isocenter of mechanical rotation.

A second acquiring sub-module 1402 is configured to acquire at least two third images.

Each of the third images may be an image obtained by performing image capture on the first positioning member.

A second determining sub-module 1403 is configured to determine a deviation of the isocenter of mechanical rotation based on first coordinates of the first positioning member in each of the third images and reference coordinates of a center point in each of the third images.

Figure 15:
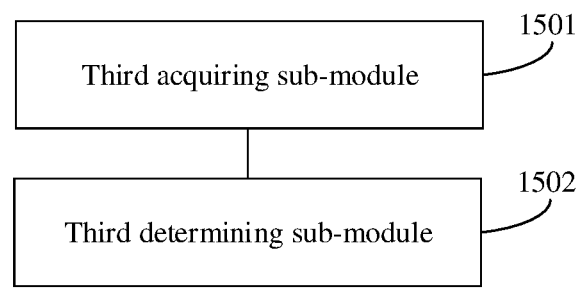
FIG. 15 is a block diagram of a third verification module in the apparatus for verifying the radiotherapy system according to an embodiment of the present disclosure.

FIG. 15 is a block diagram of a third verification module according to an embodiment of the present disclosure. As illustrated in FIG. 15, the third verification module may include the following sub-modules.

A third acquiring sub-module 1501 is configured to acquire at least two fourth images.

The fourth images are images obtained by irradiating a second positioning member disposed at a center of a third verification phantom with a beam and then performing image capture.

A third determining sub-module 1502 is configured to determine, based on each of the fourth images as obtained, actual coordinates of a beam focus, and to determine, based on the actual coordinates of the beam focus, a deviation of an isocenter of treatment from the isocenter of mechanical rotation.

Optionally, each sub-module of the first verification module, the second verification module, and the third verification module may be disposed in the same device in the radiotherapy system. For example, they may be all disposed in the control host. Alternatively, each sub-module of the first verification module, the second verification module, and the third verification module may be disposed in different devices in the radiotherapy system. For example, a first acquiring sub-module 1301 in the first verification module, a second acquiring sub-module 1402 in the second verification module, and a third acquiring sub-module 1501 in the third verification module may be all disposed in an image capture component; and a first determining sub-module 1302 in the first verification module, a second determining sub-module 1403 in the second verification module, and a third determining sub-module 1502 in the third verification module may be all disposed in an image server.

In summary, according to the apparatus for verifying the radiotherapy system provided by the embodiments of the present disclosure, as including at least one of the first verification module, the second verification module, or the third verification module that can implement different functions, the apparatus can fulfill more diverse functions.

With respect to the apparatus for verifying the radiotherapy system in the embodiments above, the specific manner of respective modules to execute the operation has been described in detail in the embodiments related to this method, and a detailed description thereof will not be repeated here.

An embodiment of the present disclosure provides a device for verifying a radiotherapy system. The device includes a processor and a memory, wherein the memory stores instructions therein, and the instructions, when loaded and executed by the processor, causes the processor to execute the method for verifying the radiotherapy system as illustrated in any one of FIGS. 10 to 12.

In addition, an embodiment of the present disclosure provides a storage medium. The storage medium stores instructions therein, and the storage medium, when being operated on a processing component, causes the processing component to execute the method for verifying the radiotherapy system as illustrated in any one of FIGS. 10 to 12.

A person skilled in the art may clearly understand that for the convenience and brevity of the description, a reference may be made to the corresponding processes in the forgoing method embodiments for the working processes of the radiotherapy system and the device for verifying the same as described above, the details of which will not be repeated here.

Described above are merely optional embodiments of the present disclosure, but are not intended to limit the present disclosure. Any modifications, equivalent replacements, improvements and the like made within the spirit and principles of the present disclosure should be included within the scope of protection of the present disclosure.

What is claimed is:

1. A device for verifying a radiotherapy system, the device comprising at least two of a first verification phantom, a second verification phantom, and a third verification phantom,
    wherein a slot for holding a film is provided in the first verification phantom, a first positioning member is disposed at a center of the second verification phantom, a second positioning member is disposed at a center of the third verification phantom, and a center point of the first verification phantom, a center point of the first positioning member and a center point of the second positioning member are coaxial.

2. The device according to claim 1, wherein the slot comprises: a first slot and a second slot; and
    wherein an insertion surface of the first slot is perpendicular to an insertion surface of the second slot, and a center point of the insertion surface of the first slot and a center point of the insertion surface of the second slot are both in coincidence with the center point of the first verification phantom.

3. The device according to claim 2, wherein an opening of the first slot and an opening of the second slot are both disposed on a first outer surface of the first verification phantom.

4. The device according to claim 3, wherein an extraction groove is provided at a junction, on the first outer surface, of the opening of the first slot and the opening of the second slot.

5. The device according to claim 2, wherein:
    the first verification phantom is provided with a first through hole for communicating an outer surface of the first verification phantom with the first slot, and a second through hole for communicating the outer surface of the first verification phantom with the second slot;
    an extending direction of the first through hole intersects with the insertion surface of the first slot, and an intersection point of the first through hole and the insertion surface of the first slot is the center point of the insertion surface of the first slot; and
    an extending direction of the second through hole intersects with the insertion surface of the second slot, and an intersection point of the second through hole with the insertion surface of the second slot is the center point of the insertion surface of the second slot.

6. The device according to claim 1, wherein an outer surface of the second verification phantom is provided with at least three sets of calibration lines, each set of the calibration lines comprises two calibration lines perpendicular to each other, an intersection point of the two calibration lines comprised in each set of the calibration lines is a target point, and the respective target points of the at least three sets of calibration lines are coplanar; and
    wherein among the at least three sets of calibration lines, two sets of the calibration lines are respectively disposed on two opposite side surfaces of the second verification phantom, and one set of the calibration lines is disposed at a surface, distal from a support that is configured to support the second verification phantom, of the second verification phantom.

7. The device according to claim 1, wherein a plurality of third positioning members are further disposed within the second verification phantom; and
    wherein the plurality of third positioning members are non-coplanar, and a number of the third positioning members is not less than 4.

8. The device according to claim 7, wherein
    distances between any two of the third positioning members are equal, and distances between each of the third positioning members and the first positioning member are equal.

9. The device according to claim 7, wherein
    the first positioning member and the third positioning members are both made of at least one of aluminum, Teflon, glass, or ceramic.

10. The device according to claim 1, wherein the third verification phantom is an internally hollow housing, within which a second positioning member pipe is disposed, and the second positioning member is disposed within the second positioning member pipe.

11. The device according to claim 1, wherein a housing of at least one of the first verification phantom, the second verification phantom, or the third verification phantom is made of organic glass.

12. The device according to claim 1, wherein the second positioning member is made of tungsten.

13. The device according to claim 1, wherein in a case where the device comprises the third verification phantom, the third verification phantom is detachably connected with the first verification phantom or the second verification phantom.

14. The device according to claim 1, comprising: the first verification phantom, the second verification phantom, and the third verification phantom, wherein
    the first verification phantom, the second verification phantom, and the third verification phantom are sequentially disposed along a length direction of a treatment couch.

15. The device according to claim 1, further comprising: a base, wherein
    at least one of the first verification phantom, the second verification phantom, or the third verification phantom is disposed on the base.

16. A radiotherapy system, comprising a device for verifying a radiotherapy system, wherein the device for verifying the radiotherapy system comprises at least two of a first verification phantom, a second verification phantom, and a third verification phantom,
    wherein a slot for holding a film is provided in the first verification phantom, a first positioning member is disposed at a center of the second verification phantom, a second positioning member is disposed at a center of the third verification phantom, and a center point of the first verification phantom, a center point of the first positioning member and a center point of the second positioning member are coaxial.

17. The radiotherapy system according to claim 16, wherein the slot comprises: a first slot and a second slot; and
wherein an insertion surface of the first slot is perpendicular to an insertion surface of the second slot, and a center point of the insertion surface of the first slot and a center point of the insertion surface of the second slot are both in coincidence with the center point of the first verification phantom.

18. A method for verifying a radiotherapy system, comprising: at least one of a first verification process, a second verification process, or a third verification process,
wherein the first verification process comprises:
acquiring a first image and a second image, wherein the first image and the second image are obtained by respectively irradiating two films inserted in slots of a first verification phantom with a beam and then scanning the two irradiated films respectively; and
determining, based on the first image and the second image, actual coordinates of a beam focus of the beam, and determining, based on the actual coordinates of the beam focus, a deviation of an isocenter of treatment from an isocenter of mechanical rotation;
wherein the second verification process comprises:
adjusting a position of a second verification phantom, such that a first positioning member disposed at a center of the second verification phantom is aligned with an isocenter of mechanical rotation;
acquiring at least two third images, wherein each of the third images is obtained by performing image capture on the first positioning member; and
determining a deviation of the isocenter of mechanical rotation based on first coordinates of the first positioning member in each of the third images and reference coordinates of a center point in each of the third images; and
wherein the third verification process comprises:
acquiring at least two fourth images, wherein the fourth images are obtained by irradiating a second positioning member disposed at a center of a third verification phantom with a beam and then performing image capture; and
determining, based on each of the fourth images as obtained, actual coordinates of a beam focus of the beam, and determining, based on the actual coordinates of the beam focus, a deviation of an isocenter of treatment from the isocenter of mechanical rotation.

19. A device for verifying a radiotherapy system, comprising:
a processor and a memory storing instructions therein, wherein the instructions, when loaded and executed by the processor, cause the processor to execute the method for verifying the radiotherapy system as defined in claim 18.

20. A non-transitory storage medium storing instructions therein, wherein the storage medium, when being operated on a processing component, causes the processing component to execute the method for verifying the radiotherapy system as defined in claim 18.

* * * * *